(12) United States Patent
Haverkost et al.

(10) Patent No.: US 11,432,821 B2
(45) Date of Patent: Sep. 6, 2022

(54) ARTERIAL-VENOUS OCCLUSION APPARATUS

(71) Applicant: Boston Scientific Scimed, Inc., Maple Grove, MN (US)

(72) Inventors: Patrick Haverkost, Brooklyn Center, MN (US); Joel Groff, Delano, MN (US); Kent Harrison, Mapple Grove, MN (US); Joseph Connolly, Minneapolis, MN (US); Gary Pederson, Albertville, MN (US); Mary-Claire Anderson, Deephaven, MN (US); David Raab, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 409 days.

(21) Appl. No.: 15/064,415

(22) Filed: Mar. 8, 2016

(65) Prior Publication Data
US 2016/0262768 A1 Sep. 15, 2016

Related U.S. Application Data

(60) Provisional application No. 62/130,375, filed on Mar. 9, 2015.

(51) Int. Cl.
*A61B 17/12* (2006.01)
*A61B 17/00* (2006.01)

(52) U.S. Cl.
CPC .... *A61B 17/12172* (2013.01); *A61B 17/0057* (2013.01); *A61B 17/12109* (2013.01); *A61B 17/12031* (2013.01); *A61B 17/12036* (2013.01); *A61B 2017/00526* (2013.01); *A61B 2017/00575* (2013.01); *A61B 2017/00592* (2013.01); *A61B 2017/00597* (2013.01); *A61B 2017/00606* (2013.01); *A61B 2017/00867* (2013.01); *A61B 2017/12054* (2013.01)

(58) Field of Classification Search
CPC ........... A61B 2017/00575; A61B 2017/00592; A61B 17/12109; A61B 17/12172
See application file for complete search history.

(56) References Cited

U.S. PATENT DOCUMENTS

| | | | |
|---|---|---|---|
| 6,911,037 B2* | 6/2005 | Gainor | A61B 17/0057 606/213 |
| 2003/0139819 A1 | 7/2003 | Beer et al. | |
| 2003/0171774 A1 | 9/2003 | Freudenthal et al. | |
| 2004/0243155 A1* | 12/2004 | Yencho | A61B 17/11 606/153 |
| 2005/0177182 A1 | 8/2005 | van der Burg et al. | |
| 2005/0273135 A1* | 12/2005 | Chanduszko | A61B 17/0057 606/213 |
| 2006/0052821 A1* | 3/2006 | Abbott | A61B 17/064 606/213 |
| 2006/0122647 A1* | 6/2006 | Callaghan | A61B 17/0057 606/213 |

(Continued)

*Primary Examiner* — Elizabeth Houston
*Assistant Examiner* — Lindsey Bachman
(74) *Attorney, Agent, or Firm* — Seager, Tufte & Wickhem, LLP (57) ABSTRACT

Expandable occlusive plugs and methods of using them are disclosed. The devices generally include a tubular body bearing multiple slits defining leaves, which expand radially outward when the ends of the device are brought toward one another.

20 Claims, 6 Drawing Sheets

(56) References Cited

U.S. PATENT DOCUMENTS

| | | | |
|---|---|---|---|
| 2007/0185529 A1* | 8/2007 | Coleman | A61B 17/0057 606/213 |
| 2008/0051830 A1* | 2/2008 | Eidenschink | A61B 17/12022 606/213 |
| 2008/0077180 A1* | 3/2008 | Kladakis | A61B 17/0057 606/216 |
| 2011/0054519 A1 | 3/2011 | Neuss | |
| 2014/0207185 A1 | 7/2014 | Goble et al. | |

* cited by examiner

FIG. 3B

ARTERIAL-VENOUS OCCLUSION APPARATUS

REFERENCE TO RELATED APPLICATIONS

This application claims priority under 35 U.S.C. § 119(e) to U.S. Provisional Application No. 62/130,375, filed Mar. 9, 2015, the entire disclosure of which is herein incorporated by reference.

FIELD OF THE INVENTION

This application relates to the field of medical devices. More particularly, the application is related to devices and methods for the occlusion of blood vessels.

BACKGROUND

Embolization involves the partial or complete occlusion of blood vessels, limiting the flow of blood therethrough. The intentional occlusion of blood vessels ("therapeutic embolization") may be used to treat a variety of vascular and non-vascular conditions including cerebral and peripheral aneurysms, ateriovenous malformation, uterine fibroids and to reduce blood flow to solid tumors including liver tumors. Embolization may be achieved by any number of means, including through the use of polymer microspheres, metal coils, metal or polymer plugs, and liquid embolic materials.

In a typical embolization procedure, local anesthesia is first given over a common artery or vein. The artery or vein is then punctured and a catheter is inserted and fluoroscopically guided into the area of interest. An angiogram is performed by injecting contrast agent through the catheter, thereby visualizing the portion of the vascular tree downstream of the distal end of the catheter. Once the catheter is positioned in a site where deposition of an embolic agent is desired, the agent is deposited through the catheter into the artery or vein to be occluded. The embolic agent is generally selected based on the size of the vessel to be occluded, the desired duration of occlusion, and/or the type of disease or condition to be treated, among others factors. Following delivery of the embolic agent to the site within the vessel to be occluded, a follow-up angiogram can be performed to determine the specificity and completeness of the occlusion.

In many embolization procedures, particularly those involving occlusion of an ostium or branch of a blood vessel with high specificity is desired. But the specificity of occlusion can be reduced by the tendency of the occlusive device or material to become displaced during deployment (termed "kickback" or "jumping" in the case of embolic coils and plugs). In the vascular occlusion setting, such kickback can result in incomplete embolization or even embolization or non-target sites. In general, occlusive plug devices tend to be less prone to kickback than embolic coils, and may be preferred in applications where kickback is particularly undesirable, but in selecting plugs vs. coils, users are presented with another tradeoff: occlusive plus such as the Amplatzer™ occlusive plugs (St. Jude Medical, Minneapolis, Minn.) generally have a larger profile than embolic coils, and are not well suited to be deployed through or into narrow or tortuous vessels.

SUMMARY OF THE INVENTION

The present invention, in its various aspects, addresses the tradeoff presented by existing coil and plug devices, providing systems and methods for single-step delivery of embolic plugs through narrow-gauge microctheters (e.g. 0.021" or 0.533 mm inner diameter (ID), compared to Amplatzer™ occlusive plug devices, which generally require catheters with a 0.035" or 0.889 mm or greater ID).

In one aspect, the present invention relates to a system for treating a patient that includes a tubular body with a sidewall that includes a plurality of cuts about its circumference. Each of the cuts extends both longitudinally and radially along a portion of the length of the sidewall, and the tubular body includes at least two circumferential regions defined by the termini of the plurality of cuts. The tubular body is moveable between an elongated configuration characterized by a first distance between the circumferential regions and a deployed configuration in which the circumferential regions are separated by a second distance less than the first distance such that a plurality of portions of the sidewall radially between the plurality of cuts are buckled or bent and displaced radially outward. In various embodiments, the sidewall optionally includes a shape memory material, the tubular body assumes the elongate configuration when radially constrained within a catheter and assumes the deployed configuration when unconstrained, and/or the tubular body includes a plurality of fibers attached thereto. The fibers, in turn, are optionally attached to an end of the tubular body. The system, optionally or additionally, includes a membrane covering at least a portion of the tubular body. The membrane can define at least one discoid shape when the tubular body is in the deployed configuration, or in certain cases, the buckled or bent sidewall portions define a plurality of leaves, at least one of which is covered by the membrane. In some cases, the membrane can include a slit, which is optionally positioned within a surface defined by one of the leaves. The membrane can be a polymer and is applied, variously, by dip coating, spray coating, or application of heat to heat-shrink tubing. In certain cases, the system also includes a guidewire and a microcatheter, and the guidewire has an outer diameter less than an inner diameter of a lumen defined by the tubular body in the elongate configuration, while the microcatheter has an inner diameter greater than an outer diameter of the tubular body in the elongated configuration but less than an outer diameter of the tubular body in the deployed configuration. The system, optionally or additionally, includes a pushrod slidably disposed within the microcatheter and having an outer diameter greater than the inner diameter of the tubular body. In some cases, the elongate body includes a structure sized and shaped to interlock with a structure on the pushrod, such as a tab or a ball. These systems may be used in medicine, and particularly for occlusion of blood vessels.

In another aspect, the present invention relates to a method of treating a patient that includes inserting a system as described above into the patient. In some cases, the step of inserting the system into a patient includes inserting the tubular body, in the elongated configuration, through a microcatheter into a body lumen (such as a blood vessel) of a patient and advancing the tubular body through a distal opening in the microcatheter. In these cases, the tubular body assumes the deployed configuration when advanced outside the microcatheter. Optionally or additionally, the system includes a guidewire and a pushrod, in which case the tubular body is advanced over the guidewire and through the microcatheter. In some instances, the system includes a pushrod, in which case the tubular body is advanced through a distal opening in the microcatheter by (a) retracting the microcatheter over the tubular body and the pushrod or (b) advancing the pushrod distally toward the distal opening of the microcatheter. In certain procedures, the method also includes the insertion of an implant into the body lumen adjacent to the tubular body. The implant is, variously, a second tubular body, an embolic coil, an embolic particle, a liquid embolic, and/or a material comprising a radioisotope such as Yttrium-90.

DRAWINGS

Aspects of the invention are described below with reference to the following drawings in which like numerals reference like elements, and wherein.

Unless otherwise provided in the following specification, the drawings are not necessarily to scale, with emphasis being placed on illustration of the principles of the invention.

DETAILED DESCRIPTION OF THE PREFERRED EMBODIMENTS

Figure 1A:
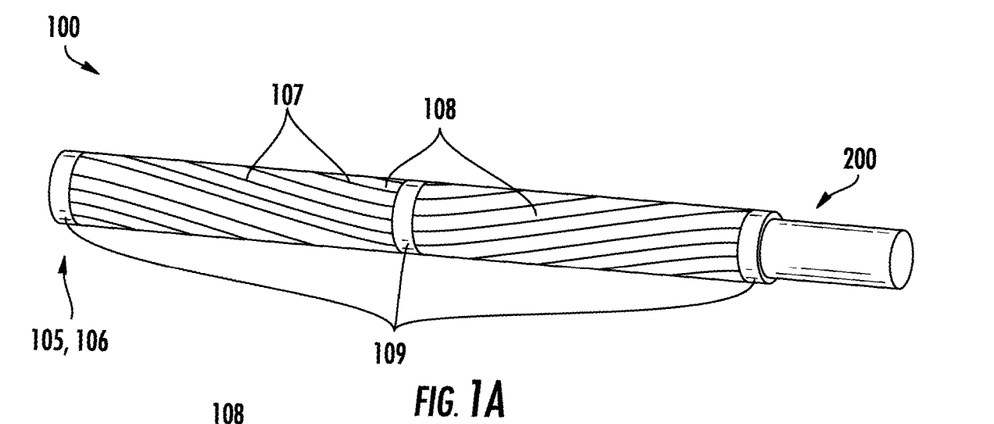
FIG. 1A through 1C shows schematic views of occlusion devices according to certain embodiments of the present invention in various stages of deployment.
Figure 1B:
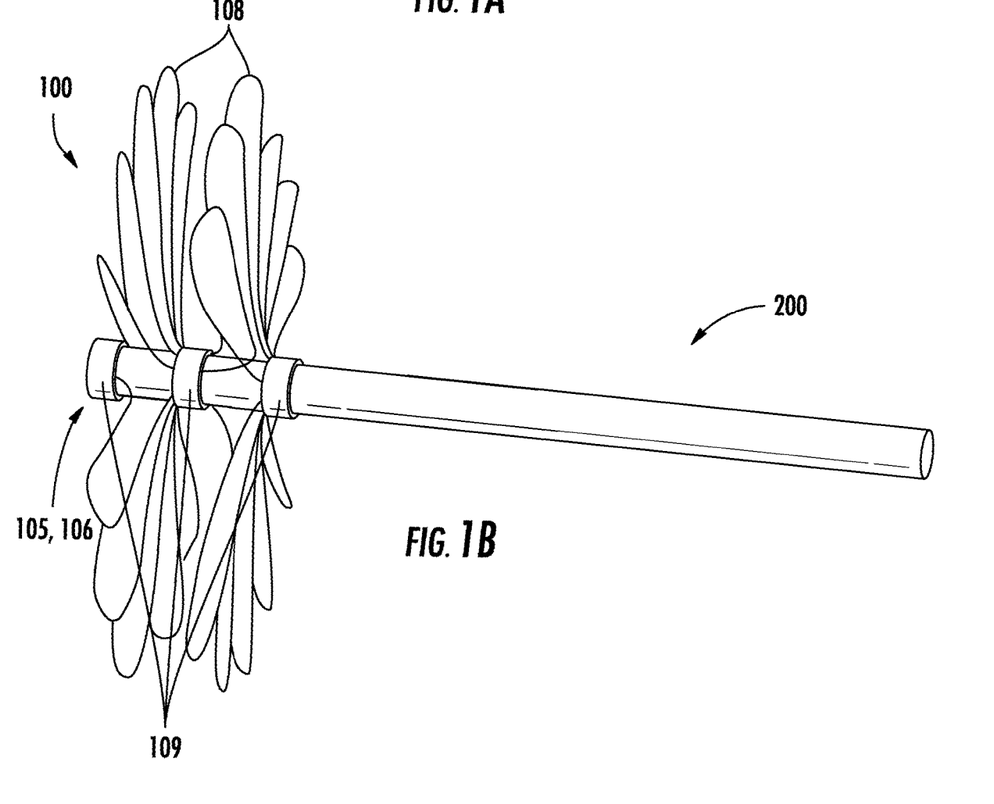

Turning to FIGS. 1A and 1B, exemplary occlusion devices 100 according to one group of embodiments of the present invention generally include one or more expandable occlusive elements 105 formed as a tubular body 106 comprising a plurality of angled, longitudinal cuts 107 about its circumference and a plurality of leaves 108 extending longitudinally between the cuts 107. The tubular body 106 also includes uncut circumferential bands 109 at the proximal and distal ends of the tubular body 106, and optionally at one or more intermediate positions along the length of the tubular body 106. The occlusive element 105 is moveable between a compressed, narrow-diameter elongated configuration, as shown in FIG. 1A, and a deployed, large diameter configuration in which the leaves 108 extend radially outwardly. This change in configurations is preferably achieved through the use of a shape memory material in the tubular body 106, most preferably nitinol, though shape memory polymers are also used in some embodiments of the present invention.

The device 100 is formed, in preferred embodiments, by laser cutting the angled longitudinal cuts 107 into the tubular body 106, thereby defining the leaves 108 and the uncut circumferential bands 109; the proximal and distal ends of the tubular body 106 are then moved toward one another (e.g. over a mandrel), deploying the leaves 108 radially outwardly, secured and heat-set such that the tubular body 106 assumes a deployed configuration when unconstrained. Among the advantages of devices 100 according to the present invention is the ability to design devices with increased deployed diameters without increasing the constrained diameter of the device; instead, the deployed diameter can be varied by changing the length of the elongate member 106 and/or the length of the longitudinal cuts 107. In addition, the hemostatic aspects of the device can be adjusted by varying the number and placement of the longitudinal cuts, which in turn varies the number and degree of twist of the leaves 108.

Figure 1C:
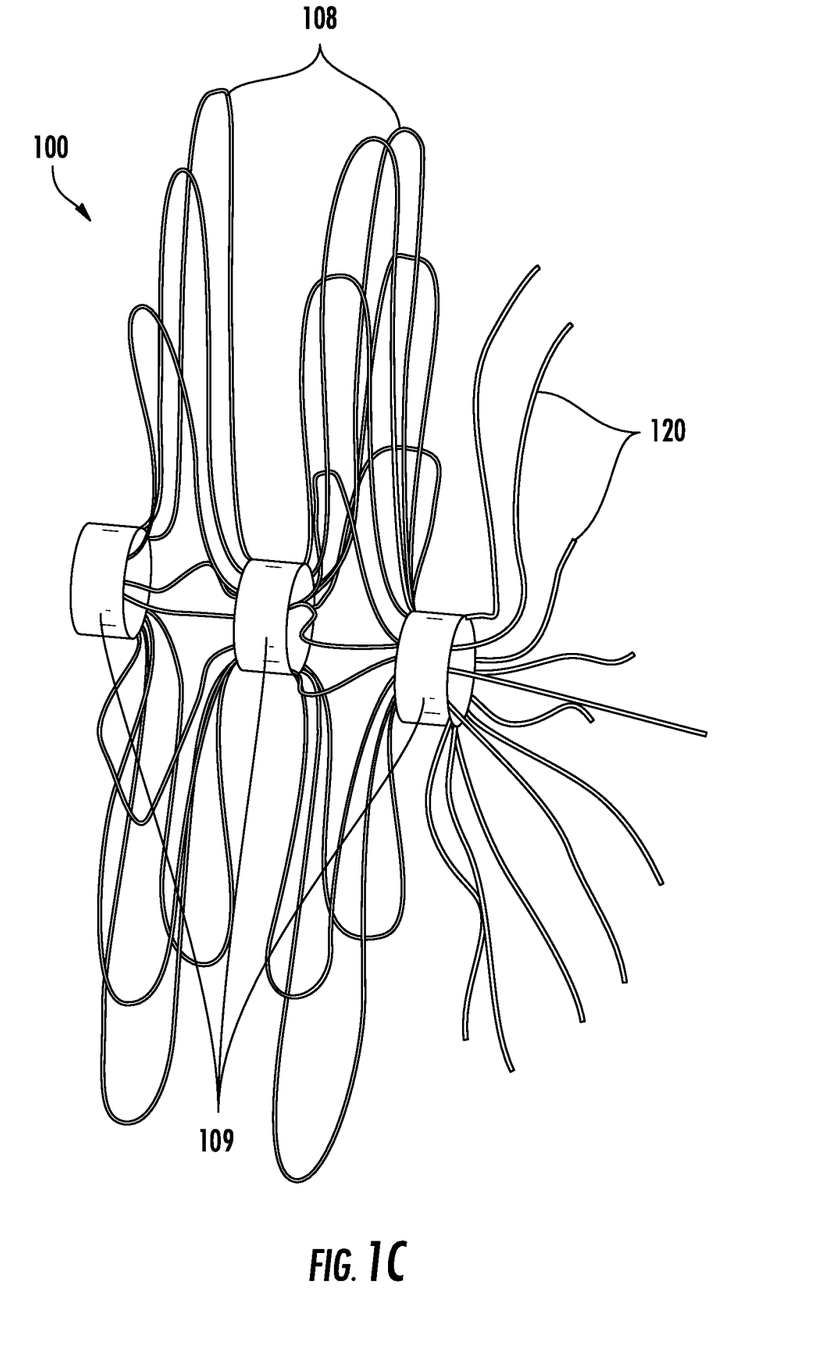

To prepare the device for deployment, e.g. within a blood vessel of a patient, the device 100 is returned to the elongated compressed configuration so that it may be fed into a microcatheter for deployment. In use, the device 100 is preferably deployed over a guidewire 200 using a microcatheter such as a 0.021"-0.027" (0.533-0.686 mm) inner-diameter torqueable microcatheter (Direxion™ microcatheter, Boston Scientific Corporation, Marlborough, Mass.) though the microcatheter can also have any suitable inner diameter, for instance as small as 0.0165" (0.419 mm) or, if a larger implant is desired, can be sized up to, for example, a 5F (0.066" or 1.667 mm) catheter. The device 100 is advanced distally through the microcatheter by means of a pushrod and may be deployed by (a) advancing the device 100 through a distal aperture of the microcatheter using the pushrod, or (b) retracting the microcatheter over the pushrod, such that the device 100 remains in the same position within the blood vessel or other body lumen where it is being deployed. Where the device 100 includes two sets of leaves 108 separated by an uncut circumferential band 109, as shown in FIGS. 1A-1C, a stepwise deployment procedure may be employed. In an exemplary deployment procedure, the distal portion of the device 100 is deployed first, while the proximal portion remains constrained within the catheter; this results in the deployment of the distal-most leaves 108, securing the device 100 within the blood vessel. Once the distal portion is deployed securely, the proximal portion can be deployed, reducing the risk of jumping or displacement of the device 100 within the lumen of the vessel. In addition, in some embodiments, such as those shown in FIGS. 3A-3B, the distal end of the elongate body 106 includes a structure that interlocks with the pushrod and requires a user action, such as advancing the device 100 through the distal end of the catheter, to detach from the pushrod.

Those of skill in the art will appreciate that the deployment procedures set forth above are similar to the procedures for deploying self-expanding stents, advantageously reducing or eliminating the need for a user to learn a unique deployment procedure or method for the present device 100. Further, devices 100 according to the various embodiments of the present invention can be deployed, then recaptured (e.g. by re-inserting the pushrod into the lumen of the tubular body 106 and, optionally, extending the microcatheter over at least part of the deployed device 100. Following recapture, the device 100 can be repositioned and re-deployed, or simply removed from the blood vessel altogether. Similarly, in some procedures, a length of vessel can be embolized by deploying a first device 100, retracting the pushrod through the catheter, and inserting another device 100 in its compressed configuration over the pushrod and through the microcatheter, then deploying it alongside the first device 100.

Figure 2A:
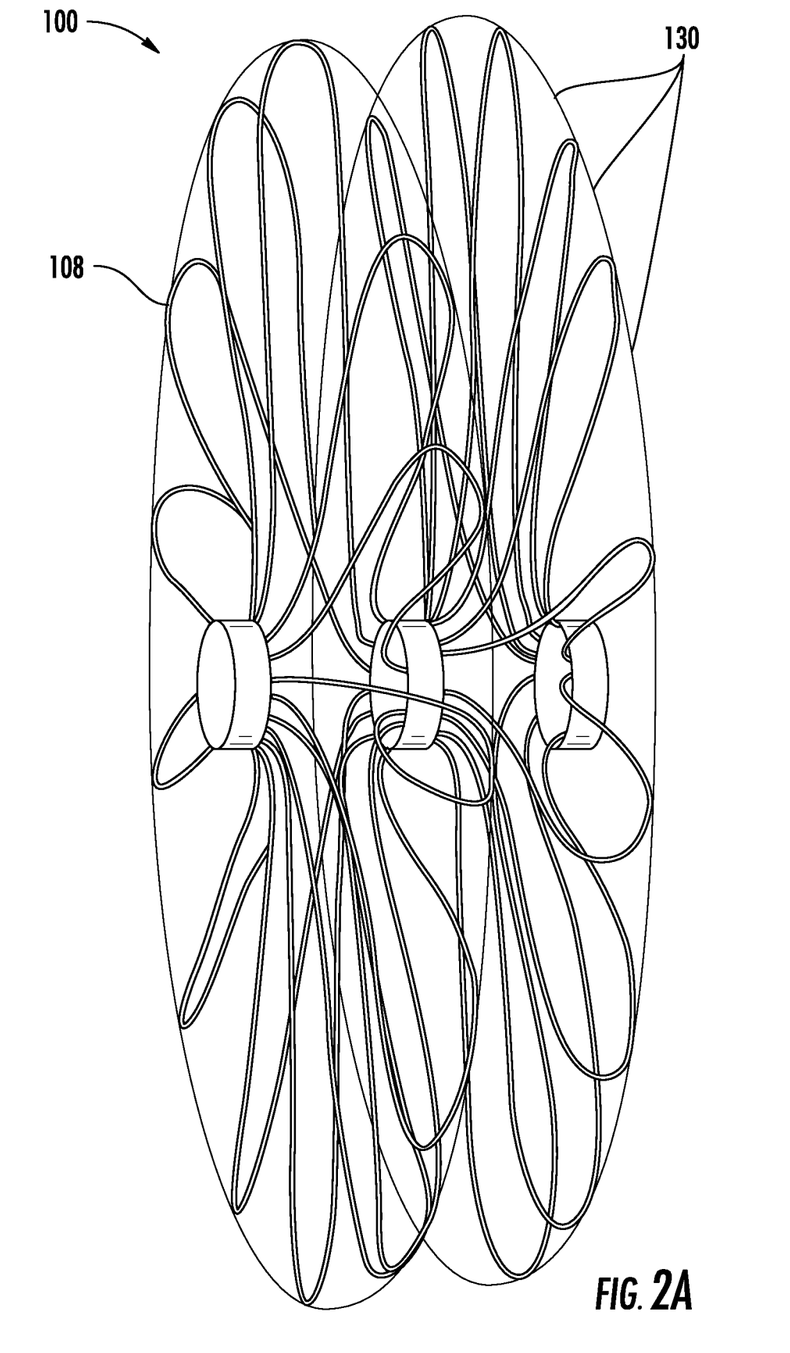
FIG. 2A through 2B shows schematic views of occlusion devices according to certain embodiments of the present invention.
Figure 2B:
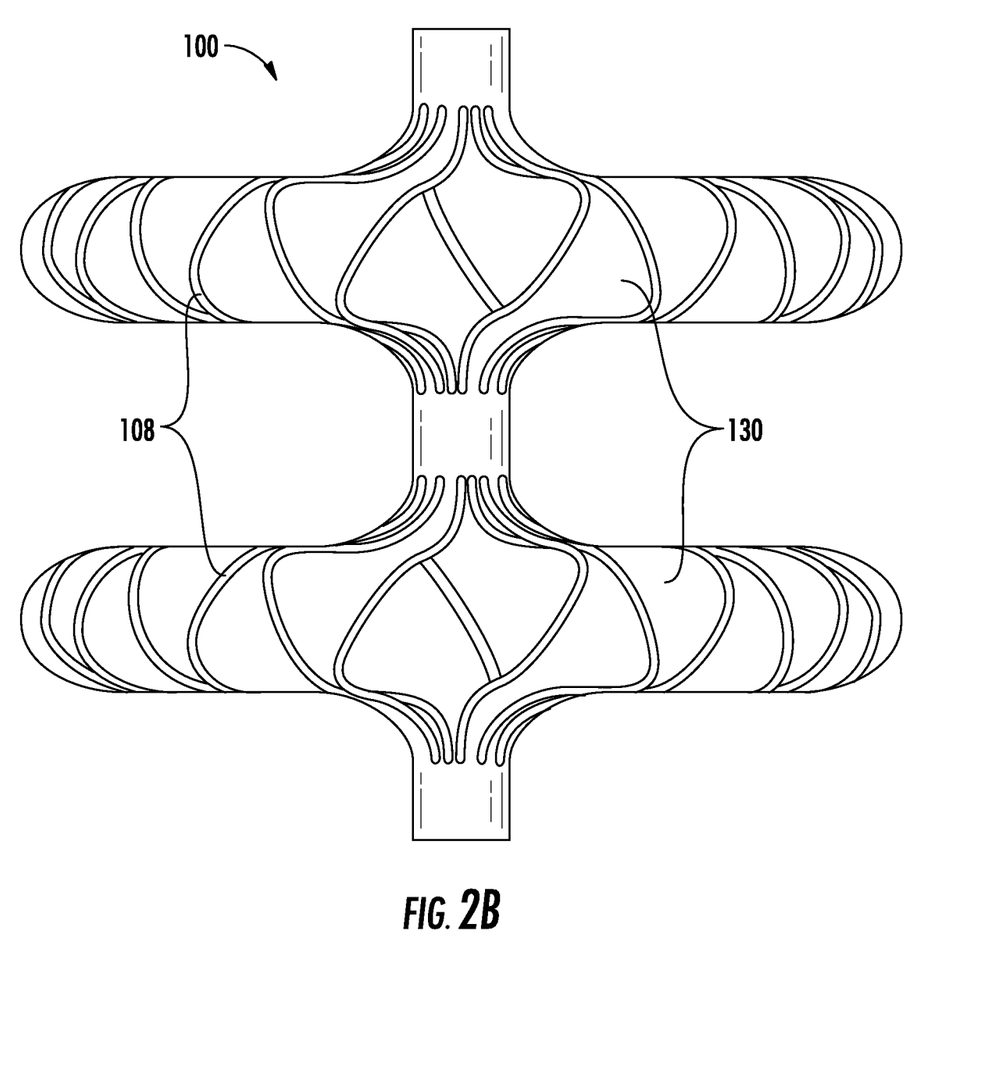
Figure 3A:
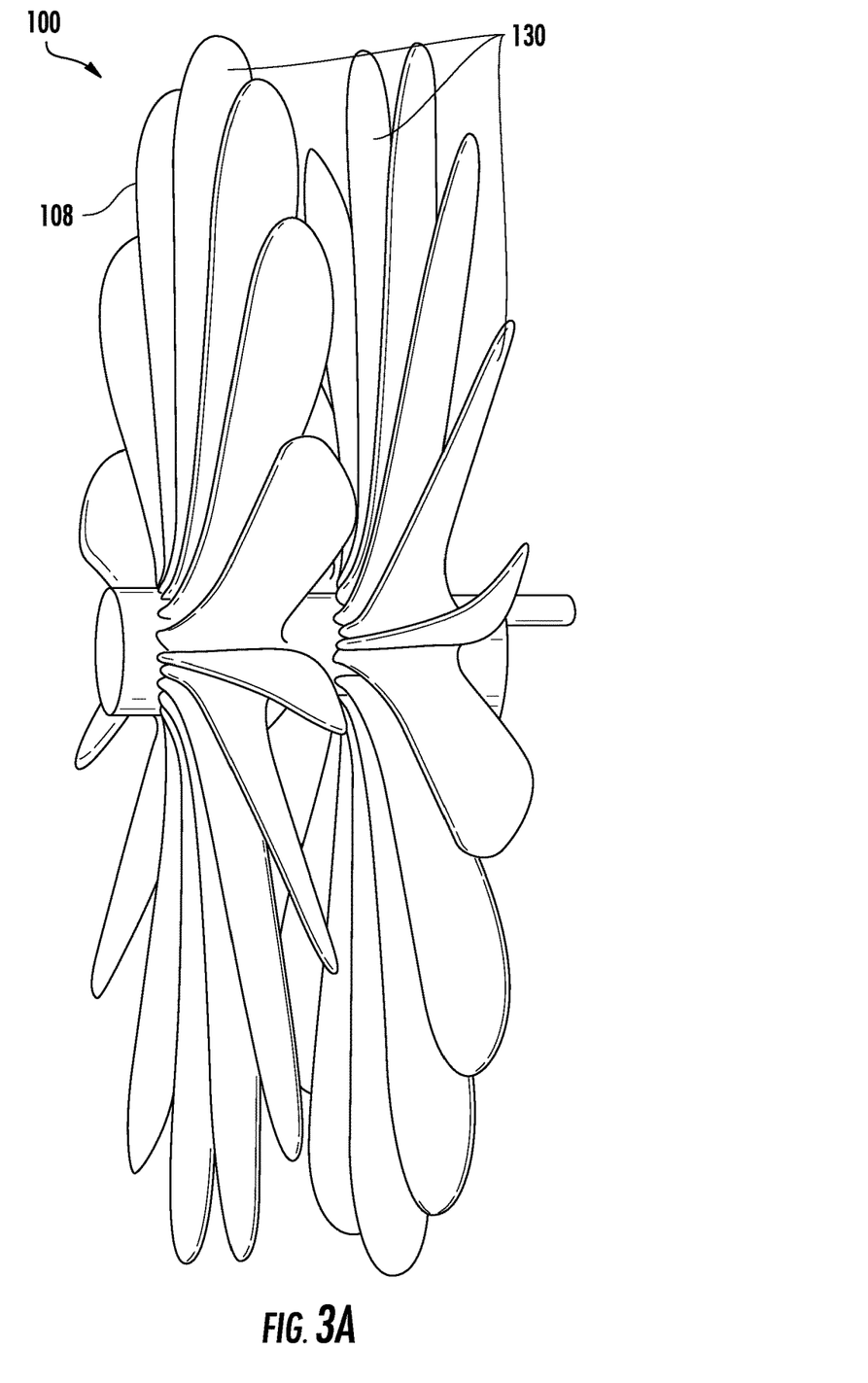
FIG. 3A through 3B shows schematic views of occlusion devices according to certain embodiments of the present invention.
Figure 3B:
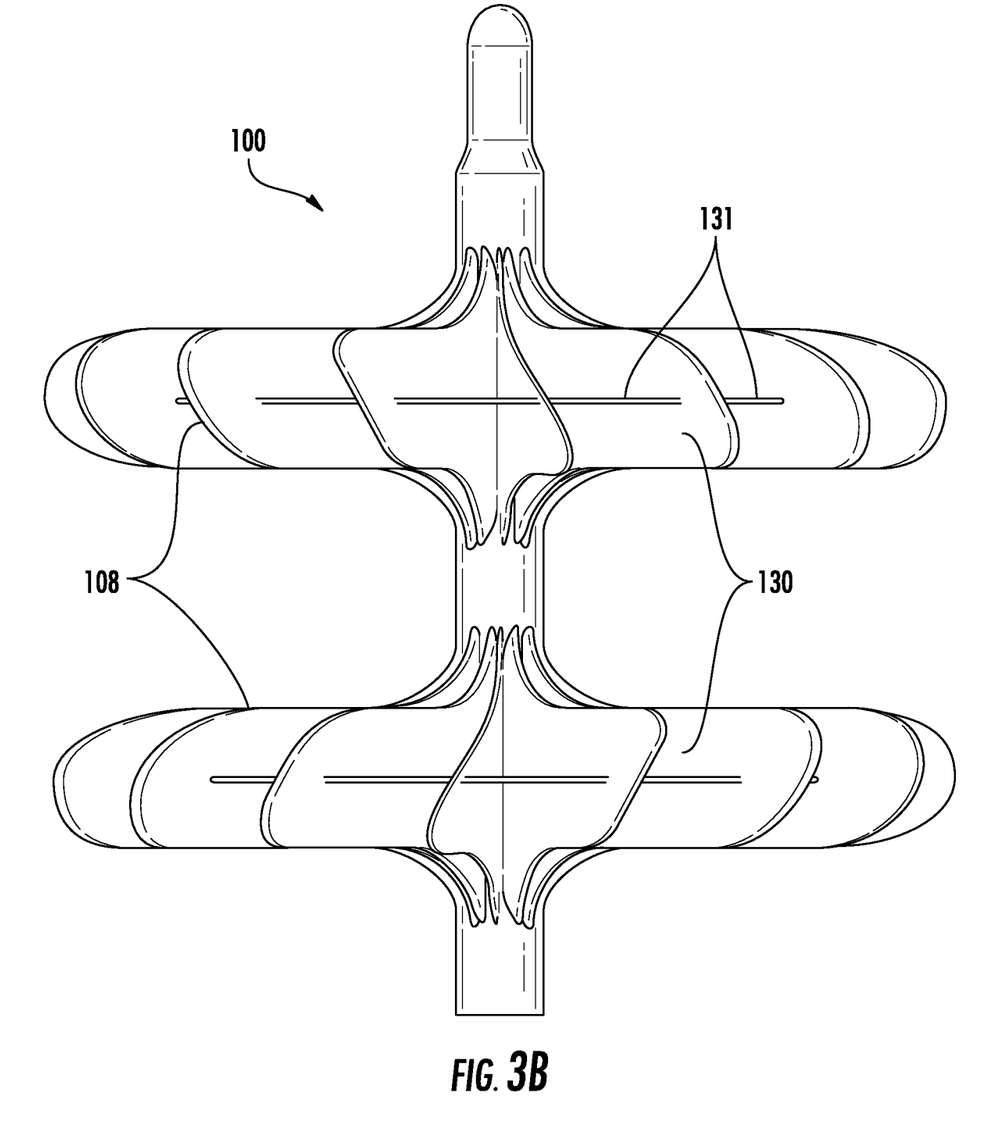

The shape and function of the device 100 is determined in large measure by the geometry of the longitudinal cuts 107 and the leaves 108, which are shown in FIGS. 1A-1C as diagonal or spiral in orientation. The length of the longitudinal cuts 107 determines the lengths of the leaves 108 and, consequently, the maximum diameter of the device 100 when deployed. Similarly, the radial offset between the proximal and distal ends of the longitudinal cuts 107 results in leaves 108 having a twist when deployed. When one or more circumferential bands 109 between longitudinal cuts 107 and leaves 108, the resulting device 100 will have two or more repeating arrays, which may be identical in terms of the length and twist of the longitudinal cuts 107 and leaves 108, or they may differ in a way that promotes clotting. In certain embodiments, the repeating arrays are offset so as to maximize turbulent flow through he deployed device 100, thereby driving clotting. For instance, in the embodiments shown in FIGS. 1A-1C, the arrays of leaves 108 twist in opposite directions when deployed, increasing turbulent flow through the deployed device 100 and contributing to blood clotting. Clotting is further improved, in some embodiments, by attaching fibers 120 as shown in FIG. 1C In some embodiments of the present invention, a membrane 103 covers at least a portion of the tubular body 106, and, when deployed, the leaves 108. For example, in one group of embodiments, illustrated in FIGS. 2A-2B, a membrane 130 extends over most or all of the device 100, and covers the exterior portions of the leaves 108, so as to form a plurality of discoid shapes extending radially outwardly. Alternatively, the membrane 130 may form propeller-like shapes as it extends over individual leaves, as shown in FIG. 3A-3B. In FIGS. 3A-3B, the membrane further includes a plurality of slits 131 In either case, membrane 130 helps disrupt the flow of blood over the device 100, thereby promoting blood clotting and occlusion of the vessel in which device 100 is deployed.

Membrane 130 can be attached to the device by any suitable means, including dip or spray coating of the device 100 in its constrained or deployed configuration, or by application of heat-shrink tubing to the elongate body 106, again in either the constrained or deployed configuration. Alternatively or additionally, the elongate body 106 may be coated (either bare or on top of the membrane 130) with one or more of (a) a pharmaceutical ingredient, such as a clotting agent (e.g. polymer-bound starch), (b) a fiber, such as a microfiber, an electrospun fiber, etc., or a fibrous matrix.

The phrase "and/or," as used herein should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The term "consists essentially of" means excluding other materials that contribute to function, unless otherwise defined herein. Nonetheless, such other materials may be present, collectively or individually, in trace amounts.

As used in this specification, the term "substantially" or "approximately" means plus or minus 10% (e.g., by weight or by volume), and in some embodiments, plus or minus 5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

Certain embodiments of the present invention have described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A system for treating a patient, the system comprising:
a tubular body having a sidewall, the sidewall including a plurality of cuts about a circumference thereof, each of the plurality of cuts extending longitudinally and radially along a portion of a length of the sidewall, the tubular body further comprising at least two circumferential regions defined by termini of the plurality of cuts,
wherein the tubular body is configured to move between an elongated configuration characterized by a first distance between the circumferential regions and a deployed configuration in which the circumferential regions are separated by a second distance less than the first distance, such that a plurality of portions of the sidewall radially between the plurality of cuts of a first of the at least two circumferential regions are buckled or bent and displaced radially outward to define a first plurality of leaves and a plurality of portions of the sidewall radially between the plurality of cuts of a second of the at least two circumferential regions are buckled or bent and displaced radially outward to define a second plurality of leaves, wherein, in the deployed configuration, each leaf of the first plurality of leaves has a degree of twist in a first orientation and each leaf of the second plurality of leaves has a degree of twist in a second orientation, the first orientation being substantially opposite to the second orientation; and
a plurality of fibers configured to promote clotting coupled to and extending proximally from a proximal end of the tubular body when the tubular body is in the deployed configuration.

2. The system of claim 1, wherein the sidewall includes a shape memory material.

3. The system of claim 1, wherein the tubular body assumes the elongated configuration when radially constrained within a catheter, and assumes the deployed configuration when unconstrained.

4. The system of claim 1, wherein each fiber of the plurality of fibers is coupled to a corresponding portion of the plurality of portions of the sidewall radially between the plurality of cuts.

5. The system according to claim 1, further comprising a membrane covering at least a portion of the tubular body.

6. The system according to claim 5, wherein the membrane defines at least one discoid shape when the tubular body is in the deployed configuration.

7. The system according to claim 5, wherein the membrane covers one or both of the first or second plurality of leaves.

8. The system according to claim 7, wherein the membrane includes a slit.

9. The system according to claim 5, wherein the membrane is a polymer applied to the tubular body by one of dip coating, spray coating, or application of heat to a heat-shrink tubing.

10. A system for treating a patient, the system comprising:
a tubular body having a sidewall, the sidewall including a plurality of cuts about a circumference thereof, each of the plurality of cuts extending longitudinally and radially along a portion of a length of the sidewall, the tubular body further comprising at least two circumferential regions defined by termini of the plurality of cuts;
a guidewire;
a microcatheter; and
a plurality of fibers configured to promote clotting coupled to and extending proximally from a proximal end of the tubular body;
wherein:
(a) the tubular body is configured to move between an elongated configuration characterized by a first distance between the circumferential regions and a deployed configuration in which the circumferential regions are separated by a second distance less than the first distance, such that a plurality of portions of the sidewall radially between the plurality of cuts of a first of the at least two circumferential regions are buckled or bent and displaced radially outward to define a first plurality of leaves, and a plurality of portions of the sidewall radially between the plurality of cuts of a second of the at least two circumferential regions are buckled or bent and displaced radially outward to define a second plurality of leaves, wherein, in the deployed configuration, each leaf of the first plurality of leaves has a degree of twist in a first orientation and each leaf of the second plurality of leaves has a degree of twist in a second orientation, the first orientation being substantially opposite to the second orientation,
(b) the guidewire has an outer diameter less than an inner diameter of a lumen defined by the tubular body in the elongated configuration,
(c) the microcatheter has an inner diameter greater than an outer diameter of the tubular body in the elongated configuration but less than an outer diameter of the tubular body in the deployed configuration;
(d) the plurality of fibers extends from the proximal end of the tubular body when the tubular body is in the deployed configuration.

11. The system according to claim 10, further comprising a pushrod slidably disposed within the microcatheter and having an outer diameter greater than an inner diameter defined by the tubular body in the elongated configuration.

12. The system according to claim 11, wherein the tubular body includes a structure sized and shaped to interlock with a structure on the pushrod.

13. The system of claim 10, wherein each fiber of the plurality of fibers is coupled to a corresponding portion of the plurality of portions of the sidewall radially between the plurality of cuts.

14. A method of treating a patient, comprising:
inserting a system into the patient, the system comprising:
a tubular body having a sidewall, the sidewall including a plurality of cuts about a circumference thereof, each of the plurality of cuts extending longitudinally and radially along a portion of a length of the sidewall, the tubular body further comprising at least two circumferential regions defined by termini of the plurality of cuts, and a plurality of fibers configured to promote clotting coupled to and extending proximally from a proximal end of the tubular body;
wherein the tubular body is configured to move between an elongated configuration characterized by a first distance between the circumferential regions and a deployed configuration in which the circumferential regions are separated by a second distance less than the first distance, such that a plurality of portions of the sidewall radially between the plurality of cuts of a first of the at least two circumferential regions are buckled or bent and displaced radially outward to define a first plurality of leaves, and
a plurality of portions of the sidewall radially between the plurality of cuts of a second of the at least two circumferential regions are buckled or bent and displaced radially outward to define a second plurality of leaves, wherein, in the deployed configuration, each leaf of the first plurality of leaves has a degree of twist in a first orientation and each leaf of the second plurality of leaves has a degree of twist in a second orientation, the first orientation being substantially opposite to the second orientation;
wherein the plurality of fibers extends from the proximal end of the tubular body when the tubular body is in the deployed configuration.

15. The method of claim 14, wherein the step of inserting the system into the patient comprises the steps of:
inserting the tubular body, in the elongated configuration, through a microcatheter into a body lumen of the patient; and
advancing the tubular body through a distal opening in the microcatheter, wherein the tubular body assumes the deployed configuration when advanced outside the microcatheter.

16. The method of claim 15, wherein the system includes a guidewire and a pushrod, and wherein the tubular body is advanced over the guidewire and through the microcatheter.

17. The method of claim 16, wherein the tubular body is advanced through the distal opening in the microcatheter by retracting the microcatheter over the tubular body and pushrod.

18. The method of claim 16, wherein the tubular body is advanced through the distal opening in the microcatheter by advancing the pushrod toward the distal opening.

19. The method of claim 16, further comprising a step of inserting an implant in the body lumen adjacent to the tubular body.

20. The method of claim 19, wherein the implant is a second tubular member, an embolic coil, an embolic particle, a liquid embolic, or a material comprising a radioisotope, or some combination thereof.

* * * * *